United States Patent [19]

Koono et al.

[11] Patent Number: 5,302,746

[45] Date of Patent: Apr. 12, 1994

[54] PROCESS FOR PRODUCING CARBOXYLIC ACID ESTER

[75] Inventors: Seiji Koono; Osamu Moriya; Toshio Noguchi, all of Niihama; Haruki Okamura, Osaka, all of Japan

[73] Assignee: Sumitomo Chemical Company, Limited, Osaka, Japan

[21] Appl. No.: 44,708

[22] Filed: Apr. 12, 1993

[30] Foreign Application Priority Data

Apr. 13, 1992 [JP] Japan .................................. 4-092639

[51] Int. Cl.$^5$ ............................................. C07C 69/52
[52] U.S. Cl. .................................... 560/205; 560/218; 560/248; 560/231; 560/103
[58] Field of Search ............... 560/205, 103, 218, 231, 560/248

[56] References Cited

U.S. PATENT DOCUMENTS 3,882,167  5/1975  Lohmar et al. ...................... 560/205
4,329,492  5/1982  Andoh et al. ....................... 560/205

FOREIGN PATENT DOCUMENTS 45-4974   2/1970   Japan .
55-22464  6/1980   Japan .
1243046  10/1986   Japan .
1-283254 11/1989   Japan .

*Primary Examiner*—Paul J. Killos
*Attorney, Agent, or Firm*—Birch, Stewart, Kolasch & Birch

[57] ABSTRACT

A process for producing a carboxylic acid ester which comprises reacting a carboxylic acid with an alcohol in the presence of an acid catalyst to produce a reaction solution and neutralizing the reaction solution, characterized by using a countercurrently contacting column for neutralization, into which the esterified reaction solution is introduced at the lower portion of the column, an aqueous strong alkaline solution at a middle portion and an aqueous weak alkaline solution at an upper portion, removing a neutralized oil phase containing the carboxylic acid ester from the top of the column and removing an aqueous phase from the bottom, thereby continuously neutralizing the reaction solution.

14 Claims, 1 Drawing Sheet

PROCESS FOR PRODUCING CARBOXYLIC ACID ESTER

BACKGROUND OF THE INVENTION

1. Field of the Invention

The present invention relates to a process for producing a carboxylic acid ester, in which acid materials present in the esterified solution produced by an esterification reaction is neutralized.

2. Description of the Related Art

Conventional processes for producing esters comprise cooling a reaction solution produced after esterification reaction to an appropriate temperature, neutralizing the esterified reaction solution with a relatively diluted aqueous solution of a strongly or weakly alkaline neutralizing agent, separating an ester phase from the aqueous phase, refining the ester phase by washing with water, removing alcohol, and distillating to produce an ester product. On the other hand, the aqueous phase was discharged from the system after an oil component present in the aqueous phase was recovered.

Specifically in the neutralizing step of the process, the produced ester may undergo hydrolysis under the highly alkaline conditions resulting in a poor yield. In order to overcome this problem, it was required to use a diluted alkaline solution and complete the neutralizing reaction within a short period of time. For this reason, depending upon the presence of catalysts at the time of esterification reaction and the type of neutralization apparatus, generally the alkaline neutralizing agent was used as an aqueous solution in the concentration of 5 to 10% by weight, which solution was used in a ratio of 0.3 to 1 by volume relative to the esterified reaction solution, thereby enhancing contact efficiency. On the other hand, excess neutralizing agents were neutralized and discarded without being recirculated and reused.

The one-pass neutralizing process using such diluted alkaline solutions as described above required a great deal of the alkaline neutralizing agents as well as a great amount of water causing loss of the alkaline neutralizing agents and an increased load of waste water, though it had a great suppressing effect on the hydrolysis reaction.

In addition, it had a disadvantages of increased production of sludge which is one of the most difficult problems in the ester production. This sludge consists of floating insolubles having a nucleus of metal compounds produced by corrosion of an apparatus at the interfaces between the ester phase and the aqueous phase at the time of the neutralizing treatment. When a larger amount of the sludge was produced, separability between the oil phase and the aqueous phase was quite diminished after the neutralization so that the waste water entailed a greater amount of the oil component resulting in a loss of ester as well as an increased load of waste water. In order to avoid this difficulty, the prior art techniques required a step of removing the oil component from the water phase by filtration or extraction with solvents.

An attempt has been proposed to improve the neutralization step as disclosed in, for example, Japanese Patent KOKOKU (Post-Exam.) No. Sho 45-4974, where in the first stage, a proportion of 80 to 90% of the acid component present in the reaction solution after the esterification is neutralized with an aqueous solution of caustic soda or caustic potash having a concentration of 2 to 5% by weight with sufficiently mixing for a retention time of one minute or less, and then in the second stage, to the resultant mixture an aqueous solution of sodium carbonate or sodium bicarbonate having a concentration of 4 to 12% by weight is added with sufficiently mixing for a retention time of one minute or less to complete the neutralization of the acid component in the reaction solution. In this method, it is possible to some extent to suppress both the reduction in contact efficiency due to foaming with carbonic acid gas and the loss of the once produced ester due to the hydrolysis thereof. However, the neutralization step is complicated and in addition, such method is essentially the same in that a higher level of the alkaline neutralizing agent and a great amount of water are again required.

We have made an intensive research for novel process for neutralization capable of overcoming the problems of the prior art neutralization process using larger amounts of a diluted aqueous alkaline solution and water. As a result, we have found that the problems can be solved by using a countercurrently contacting column for neutralization, into which an aqueous strong alkaline solution and an aqueous weak alkaline solution are introduced at a middle portion and an upper portion, respectively, and contacted countercurrently with a reaction solution introduced at the bottom portion of the column, from which the present invention resulted.

SUMMARY OF THE INVENTION

The present invention is a process for producing a carboxylic acid ester which comprises reacting a carboxylic acid with an alcohol in the presence of an acid catalyst to produce a reaction solution and neutralizing the solution, characterized by using a countercurrently contacting column for neutralization, into which the esterified reaction solution is introduced at the bottom portion of the column, an aqueous strong alkaline solution at a middle portion and an aqueous weak alkaline solution at an upper portion, removing a neutralized oil phase containing the carboxylic acid ester from the top of the column and removing an aqueous phase from the bottom, thereby continuously neutralizing the reaction solution.

DETAILED DESCRIPTION OF PREFERRED EMBODIMENTS

Figure 1:
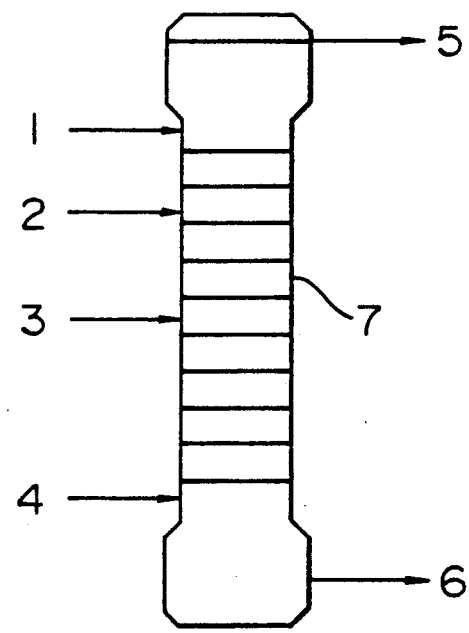
FIG. 1 is a schematic cross-sectional view of an embodiment of the column to be used in the present invention, in which 1 designates a feed line for washing water, 2 a feed line for an aqueous weak alkaline solution, 3 a feed line for an aqueous strong alkaline solution, 4 a feed line for an esterified reaction solution, 5 a line for removing a neutralized oil phase, 6 a line for removing a aqueous phase and 7 a countercurrently contacting column.

Carboxylic acids to be used in the present invention are not critical in so far as produced esters are soluble in the solutions or solvents and include, for example, acetic acid, propionic acid, acrylic acid, methacrylic acid, benzoic acid and the like. The similar thing can apply to alcohols, and for example, methanol, ethanol, propanol, butanol, 2-ethylhexanol and the like may be mentioned.

The term "acid materials" present in the esterified reaction solution as used here refers to the unreacted carboxylic acid present in the reaction solution produced from the esterification and the sulfuric acid used as an esterification catalyst.

The alkaline neutralizing agents to be used in the present invention are not critical so far as they are water soluble alkaline materials. Caustic soda, caustic potash, and the like as strong alkaline materials, and sodium carbonate, sodium bicarbonate, potassium carbonate, potassium bicarbonate and the like as weak alkaline materials may be mentioned. The aqueous strong alkaline solutions and the aqueous weak alkaline solutions should have a concentration in the range of about 1 to 10% by weight, preferably 2 to 5% by weight. If the concentration is lower than about 1% by weight, the amount of waste water is increased, while if it is higher than about 10% by weight, the hydrolysis reaction of the ester is undesirably increased.

The temperature for neutralization is in the range of about 10° to 80° C., preferably in the range of 20° to 60° C. The temperature lower than about 10° C. causes an increase in viscosity of the solutions resulting in insufficient contact between the esterified reaction solution and the aqueous alkaline solution and then resulting in poor separation of the oil phase from the aqueous phase. The temperature exceeding about 80° C. enhances the hydrolysis reaction as well as the amount of the oil component dissolving into the aqueous phase resulting in a unit deterioration.

The ratio of the amount of the neutralizing agent to that of the esterified reaction solution to be introduced is determined so as to result in an addition of an equivalent amount of the alkaline materials to that of the acids in the reaction solution. The ratio of the strong alkaline material to the weak alkaline material to be added as neutralizing agents should be preferably in the range of 1:025 to 0.4 by equivalent. If higher proportions of the strong alkaline materials than that range are used, proceeding of the hydrolysis reaction is facilitated, while if higher proportions of the weak alkaline materials than that range are used, generation of carbonic acid gas is increased resulting in poor separation between the oil phase and the aqueous phase.

The amount of the esterified reaction solution and/or that of the aqueous alkaline solution to be supplied are adjusted so as to achieve a pH in the range of about 2 to 7, preferably 3 to 4 of the aqueous phase removed at the bottom of the column. A pH of less than about 2 is undesirable because of an reduction in the rate of neutralization for the acid components and problems of structural materials. A pH of higher than about 7 facilitates the hydrolysis reaction resulting in a reduced yield of ester.

According to the present invention, the esterified reaction solution is introduced at the lower portion of the countercurrently contacting column, and the aqueous strong alkaline solution is introduced at the middle portion thereof, allowing the zone lower than the level of the introduction of the aqueous strong alkaline solution to have effects of neutralization and washing, so that there can be recovered a neutralized aqueous phase in the state where the catalytic acid component has been neutralized and the unreacted carboxylic acid has not been neutralized. It is possible to recover the carboxylic acid from the aqueous phase separately. By supplying the aqueous weak alkaline solution at the upper portion of the column and effecting the neutralization therewith, the hydrolysis of the ester can be suppressed to a ratio of 0.3% or less.

Water for washing the oil phase may be introduced at a level higher than that of the introduction of the aqueous weak alkaline solution in order to minimize the quantities of the alkaline component and the salts produced by the neutralization which are entrained in the discharged oil phase. All the water flows downward so that either of the weak alkaline solution or the strong alkaline solution can be used directly in a higher concentration. The amount of the washing water to be supplied is generally in the range of about 15 to 20% by volume of the esterified reaction solution. Depending upon the type of ester, no washing water may be supplied with the alkaline materials and the like being scarcely entrained in the oil phase.

As countercurrently contacting column for neutralization, any one of multi-stage countercurrently contacting columns for neutralization to be used for ordinary extraction such as pulse column with perforated plates, rotary disk column, packed column and sieve tray column may be employed. Thus, the neutralization column is not critical so long as good liquid-liquid dispersion can be accomplished, and preferred one is capable of enhancing the liquid-liquid dispersion by pulsing. The pulsing can achieved by supplying the esterified reaction solution by a plunger pump. It may be conducted by using a tower with perforated plates being vibrated up and down.

The retention time of the solutions has a great influence on the efficiency of neutralization as well as on the separability between the oil phase and the aqueous phase. The retention times of the esterified reaction solution and the aqueous alkaline solution are generally on the order of 0.05 to 0.1 hours. If the velocity of the solutions to be supplied is too high, the size of dispersed droplets becomes larger and the retention time is shortened to reduce the neutralization efficiency. Conversely, if the velocity of the solutions to be supplied is too low, the longer retention time leads to facilitation of the hydrolysis reaction of the ester.

The present invention will be described with reference to drawings. FIG. 1 is a schematic cross-sectional view of an embodiment of the column to be used in the present invention. The esterified reaction solution is introduced into a countercurrently contacting column 7 through a line 4. The aqueous strong alkaline solution is supplied through a line 3, the aqueous weak alkaline solution through a line 2, and the washing water through a line 1. The oil phase, from which acid components were removed by washing with neutralization, overflows and is removed through a line 5, While the aqueous phase containing the salts produced by the neutralization is removed through a line 6. This removed aqueous phase may be recirculated to be used for all or a part of the washing water.

The present invention allows the neutralization of the esterfied reaction solution to be accomplished with minimizing loss of alkaline materials and the hydrolysis reaction of produced ester, so that carboxylic acid esters can be obtained without reducing the ester yield. Moreover, facility can be very compacted.

The present invention will be in more detail with reference to the following examples, without being limited thereto.

EXAMPLE 1

Using a column with perforated plates as a countercurrently contacting column for neutralization, neutralization of an esterified reaction solution was performed.

The perforated plate column had ten plates of 60 mm$\phi$ × 1000 mmH having perforations of a pore size of 4 mm$\phi$ and a porosity of 20% and a theoretical number of stages corresponding to 3.5.

50 kg/h of an esterified reaction solution produced by esterification of n-butanol with acrylic acid in the presence of sulfuric acid as catalyst containing 79.7% by weight n-butyl acrylate, 15.8% by weight n-butanol, 0.6% weight acrylic acid, 2.7% by weight high boiling point components, 1.0% by weight sulfuric acid, and trace dibutyl ether were introduced into the aforementioned countercurrently contacting column at the lower portion thereof.

On the other hand, 9.0 kg/h of an aqueous 2% by weight caustic soda solution were introduced at the middle portion and 4.2 kg/h of an aqueous 2% by weight sodium carbonate solution were introduced at the upper portion of the neutralization column. The distances between the adjacent introduction levels were the same corresponding to a theoretical number of stages of 1.7. Liquid-liquid dispersion was achieved by giving pulsed vibration at the bottom portion with a plunger pump. The pulsed vibration was set at a vibration frequency of 72 rpm and a vibration amplitude of 30 mm. With respect to temperatures, the aqueous solution of caustic soda was supplied at 32° C., the aqueous solution of sodium carbonate was at 25° C., and the esterified reaction solution was at 42° C.

Continuous neutralization was conducted under the conditions of a retention time of 0.06 to 0.07 hour with a neutralized oil phase being removed at the top of the column at a rate of 50 kg/h and a neutralized aqueous phase being removed at the bottom of the column at a rate of 13.2 kg/h. The pH of the aqueous phase was 3.8, the amount of the acid components in the oil phase was 10 ppm or less and that of sodium ions was 0.5 ppm or less. The oil phase easily separated from the aqueous phase, and no sludge and no carbon dioxide were generated. The rate of hydrolysis of the ester was on the order of 0.2%.

COMPARATIVE EXAMPLE 1

Using an one liter glass vessel with a stirrer and a jacket, neutralization and washing were batchwise performed. 250.2 g of an esterified reaction solution comprising 77.6% by weight n-butyl acrylate, 18.1% by weight n-butanol, 1.2% weight acrylic acid, 2.1% by weight high boiling point components, 1.0% by weight sulfuric acid, and a trace of dibutyl ether were charged into the vessel, to which 108.3 g, i.e, equivalent amount of an aqueous 2% by weight caustic soda solution were added and mixed, followed by stirring at a temperature of 70° C. at 500 rpm for 0.5 hour. After standing for 0.3 minute, phase separation occurred to produce 238.9 g of an oil phase and 105.5 g of an aqueous phase. The pH of the aqueous phase removed was 5.3, and the oil phase contained 0.25% by weight of acrylic acid. The rate of hydrolysis of the ester was about 1%.

EXAMPLE 2

An esterified reaction solution produced by esterification of 2-ethylhexanol with acrylic acid in the presence of sulfuric acid as catalyst comprising 72.9% by weight 2-ethylhexyl acrylate, 22.8% by weight 2-ethylhexanol, 0.34% by weight acrylic acid, 3.7% by weight high boiling point components, and 1.0% by weight sulfuric acid was neutralized in the same procedure as in Example 1.

The esterified reaction solution was supplied at a rate of 49 kg/h, an aqueous 2% by weight caustic soda solution at 9.9 kg/h, an aqueous 2% by weight sodium carbonate solution was at 4.6 kg/h. A neutralized oil phase was removed at a rate of 47.8 kg/h and a neutralized aqueous phase was removed at a rate of 17.2 kg/h.

The pH of the aqueous phase was 2.0, the amount of the acid components in the oil phase was 200 ppm and that of sodium ions was 1 ppm. A washing water was supplied at a level higher than that of the introduction of the aqueous weak alkaline solution at a rate of 8.2 kg/h, whereby the acid was reduced to about 50 ppm and the concentration of sodium ions was reduced to 0.2 ppm.

What is claimed is:

1. A process for producing a carboxylic acid ester which comprises reacting a carboxylic acid with an alcohol in the presence of an acid catalyst to produce a reaction solution and neutralizing the reaction solution, characterized by using a countercurrently contacting column for neutralization, into which the esterified reaction solution is introduced at the lower portion of the column, an aqueous strong alkaline solution at a middle portion and an aqueous weak alkaline solution at an upper portion, removing a neutralized oil phase containing the carboxylic acid ester from the top of the column and removing an aqueous phase from the bottom, thereby continuously neutralizing the reaction solution.

2. The process for producing a carboxylic acid ester according to claim 1, wherein a washing water is supplied at a level higher than that of the introduction of said aqueous weak alkaline solution at the upper portion of the countercurrently contacting column for neutralization.

3. The process for producing a carboxylic acid ester according to claim 1 or claim 2, wherein said countercurrently contacting column for neutralization is a pulse column with perforated plates, sieve tray column, or a rotary disk type column.

4. The process for producing a carboxylic acid ester according to claim 1, wherein said strong alkaline material is caustic soda and said weak alkaline material is sodium carbonate.

5. The process for producing a carboxylic acid ester according to claim 1, wherein said aqueous strong alkaline solution and said aqueous weak alkaline solution have an concentration of about 1 to 10% by weight.

6. The process for producing a carboxylic acid ester according to claim 1, wherein a ratio of said aqueous strong alkaline solution and said aqueous weak alkaline solution to be added is in the range of 1:0.25 to 0.4 by equivalent.

7. The process for producing a carboxylic acid ester according to claim 2, wherein said countercurrently contacting column for neutralization is a pulse column with perforated plates, sieve tray column, or a rotary disk type column, and wherein said strong alkaline material is caustic soda and said weak alkaline material is sodium carbonate.

8. The process for producing a carboxylic acid ester according to claim 7, wherein said aqueous strong alkaline solution and said aqueous weak alkaline solution have a concentration of about 1 to 10% by weight.

9. The process for producing a carboxylic acid ester according to claim 7, wherein a ratio of said aqueous strong alkaline solution and said aqueous weak alkaline solution to be added is in the range of 1:0.25 to 0.4 by equivalent.

10. The process for producing a carboxylic acid ester according to claim 1, wherein said carboxylic acid is selected from the group consisting from acetic acid, propionic acid, acylic acid, methacrylic acid and benzoic acid, and wherein said alcohol is selected from the group consisting of methanol, ethanol, propanol, butanol and 2-ethyhexanol.

11. The process for producing a carboxylic acid ester according to claim 7, wherein said carboxylic acid is selected from the group consisting from acetic acid, propionic acid, acylic acid, methacrylic acid and benzoic acid, and wherein said alcohol is selected from the group consisting of methanol, ethanol, propanol, butanol and 2-ethyhexanol.

12. The process for producing a carboxylic acid ester according to claim 1, wherein said aqueous strong alkaline solution and said aqueous weak alkaline solution have a concentration of about 2 to 5% by weight.

13. The process for producing a carboxylic acid ester according to claim 1, wherein the reaction solution is neutralized at a temperature in the range of about 10° to 80° C.

14. The process for producing a carboxylic acid ester according to claim 1, wherein the esterified reaction solution is retained in said column for a retention time period of 0.05 to 0.1 hours.

* * * * *